(12) United States Patent
Van Beek et al.

(10) Patent No.: US 7,486,978 B2
(45) Date of Patent: Feb. 3, 2009

(54) CATHETER HEAD

(75) Inventors: Michael Cornelis Van Beek, Eindhoven (NL); Coen Theodorus Hubertus Fransiscus Liedenbaum, Eindhoven (NL); Gerhardus Wilhelmus Lucassen, Eindhoven (NL); Wouter Harry Jacinth Rensen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 137 days.

(21) Appl. No.: 10/554,352

(22) PCT Filed: Apr. 23, 2004

(86) PCT No.: PCT/IB2004/050498

§ 371 (c)(1),
(2), (4) Date: Oct. 24, 2005

(87) PCT Pub. No.: WO2004/093669

PCT Pub. Date: Nov. 4, 2004

(65) Prior Publication Data

US 2007/0010727 A1      Jan. 11, 2007

(30) Foreign Application Priority Data

Apr. 24, 2003 (EP) .................................. 03101135

(51) Int. Cl.
*A61B 5/1455* (2006.01)

(52) U.S. Cl. ........................ 600/341; 600/310; 600/322

(58) Field of Classification Search ............. 600/310, 600/322, 341, 342; 604/6.08, 66
See application file for complete search history.

(56) References Cited

U.S. PATENT DOCUMENTS

| | | | |
|---|---|---|---|
| 3,807,390 A | | 4/1974 | Ostrowski et al. |
| 3,848,580 A | * | 11/1974 | Hyden et al. .................. 600/310 |
| 4,622,974 A | | 11/1986 | Coleman et al. |
| 4,832,483 A | * | 5/1989 | Verma ........................... 356/39 |
| 5,104,392 A | * | 4/1992 | Kittrell et al. ................. 606/15 |
| 5,615,673 A | | 4/1997 | Berger et al. |
| 5,628,890 A | * | 5/1997 | Carter et al. ............ 204/403.05 |
| 5,938,582 A | | 8/1999 | Ciamacco et al. |
| 5,993,378 A | | 11/1999 | Lemelson |
| 6,208,887 B1 | | 3/2001 | Clarke |
| 6,240,312 B1 | | 5/2001 | Alfano et al. |
| 6,302,866 B1 | | 10/2001 | Marggi |

FOREIGN PATENT DOCUMENTS

WO     WO 01/97902 A2     12/2001

* cited by examiner

*Primary Examiner*—Eric F Winakur
*Assistant Examiner*—Etsub D Berhanu

(57) ABSTRACT

The present invention relates to a catheter head comprising: means (104, 108; 306, 304; 320; 322; 326; 338) for directing of radiation to a blood detection volume (220; 310), means (104, 108; 306, 304; 320; 322; 326; 332, 334, 330; 338) for receiving of return radiation from the blood detection volume, means (104; 306; 330) for transmitting of the return radiation to means (122) for analysis of the return radiation for determination of at least one property of the blood.

19 Claims, 7 Drawing Sheets

CATHETER HEAD

FIELD OF THE INVENTION

The present invention relates to the field of catheters and imaging systems for catheterisation.

BACKGROUND AND PRIOR ART

Catheterisation provides effective and quality service in significantly reducing patient discomfort, hospital stay, and medical cost. It often requires the ability to enter the vascular system through very small incisions and to manoeuvre therapeutic or diagnostic devices to the target region in a human body. With the smallest possible circular cross-sections, catheters are the most important device widely used in interventing procedures. More than any other type of interventing device, catheters are extremely diverse in shape and specific features. Each catheter is designed for its own purpose and is distinct from others with its own characteristics and configuration.

The term catheter as used herein refers to any type of invasive surgical tool, used for insertion into a human or animal body for the purpose of providing remote access to a part of the body for performing some type of investigative and/or medical procedure.

U.S. Pat. No. 6,208,887B1 shows a catheter-delivered low resolution Raman scattering analysing system for detecting lesions of a subject. The system uses a multi-mode laser attached to a catheter in making in-vivo Raman spectroscopic measurements of the lesion. The system includes a light collector and a light dispersion element as well as a detector to measure spectral patterns that indicate the presence of a lesion. In addition the components of the lesion can also be identified based on the unique Raman spectrum associated with each component of the lesion.

Further, various catheter tracking techniques for remotely locating and tracking a catheter inside a human or animal body are known from the prior art. Currently, X-ray fluoroscopic imaging is the standard catheter tracking technique. For example the Philips Cath-Lab systems provide X-ray imaging during catheterisation for monitoring of the operation. (http://www.medical.philips.com/main/products/cardiovascular/)

For example, in catheter based surgery a long and narrow plastic tube is inserted into the artery in the groin or arm. The physician then leads the catheter through the main artery to the heart During heart catherisation, the following diagnostic measurements can be made:
  A small amount of contrast dye can be injected via the catheter. This contrast allows the blood vessels and heart chambers or valves, to be viewed using X-rays.
  The pressure inside the heart chambers can be measured.
  The concentration of oxygen and carbon dioxide in the blood can be measured locally.
  The electrical signals inside the heart can be measured, or the response to applied electrical signals can be determined.
Catheter based treatments include:
  PTCA (percutane transluminale coronaire angioplasty) to widen the blood vessel locally.
  Placement of an endovascular prostheses in the blood vessel.

Typically various medical parameters are measured and monitored during catheterisation, such as heart frequency, blood pressure and others. This medical information is essential for permanently monitoring the state of the patients body.

There is therefore a need for a catheter head enabling an improved monitoring of the state of a patient's body during catheterisation.

SUMMARY OF THE INVENTION

The present invention provides for a catheter head which enables in vivo determination of at least one blood property by directing of radiation to a blood detection volume and analysing of return radiation which is returned from a blood detection volume.

For example the catheter head has an optical wave guide for guiding radiation, such as laser radiation or infrared radiation, to a blood detection volume which is located in front of the catheter head; alternatively the blood detection volume can be located within an inlet or cavity inside the catheter head or at another suitable location. Radiation which is returned from the blood detection volume in response is captured by the catheter head and transmitted to an analyser. On the basis of the analysis of the return radiation at least one property of the blood is determined.

In accordance with a preferred embodiment of the invention Raman spectroscopy is utilized. Laser radiation is directed into a blood detection volume which is located in front of or inside the catheter head. The resulting Raman scattered radiation is transmitted to a spectroscope for analysis of the Raman spectrum in order to determine one or more properties of the blood.

Raman spectroscopy is based on inelastic scattering of light on molecules. In this scattering process, energy is transferred between the photon and the molecule, resulting in a wavelength shift of the light. The energy corresponding to the wavelength shift is equal to the energy difference of vibrational states of the molecule.

By detecting the Raman signal in a sufficiently large wavelength region, the energy of a large number of molecular states can be calculated. Because this combination of energies is specific for each molecule, the Raman spectrum can be considered as a fingerprint of a molecular species. Blood analytes—for example glucose or lactate—can be detected using Raman spectroscopy. These analytes provide general and specific information about the patient's health.

The integration of a Raman probe into a catheter in accordance with the present invention has the advantage, that blood analysis can be permanently performed during catheterisation for improved monitoring of the medical state of the patient during the operation. For example, this diagnostic tool can be used during catheterisation for the following purposes:
  monitoring of the catheterisation procedure, for example by continuous monitoring of the patient's health by measurement of oxygenation or lactate;
  measurement of local blood composition.

This compares to prior art blood analysis, where blood is drawn from the arm using a needle and the blood sample is analysed in a chemical laboratory. This analysis and the transport take a considerable amount of time, varying between two days and typically 20 minutes in emergency situations. In contrast the present invention enables to continuously monitor the properties of the blood which provides the physician with up to date information on the medical state of the patient.

In accordance with a preferred embodiment of the invention, confocal Raman spectroscopy using optical wave guides is used. Light from the Raman excitation laser is coupled into an optical fibre and this fibre is incorporated into the catheter. In the catheter head, light from the fibre is collected by a lens and is focused into the detection area. Raman scattered light is collected by the same objective and coupled back into the optical fibre. The endpoint of the fibre serves as a pinhole to ensure confocal detection.

In accordance with a further preferred embodiment two separate optical fibers are used: One optical fibre for transmitting the incident light to the blood detection volume and one for the return radiation.

In accordance with a further preferred embodiment of the invention, a lens is used having a high numerical aperture (NA) in order to collect as much Raman scattered radiation as possible. The collected Raman light travels back through the optical fibre and is detected by a spectrum analyser to yield quantitative concentration measurements of the detected analyte(s).

In accordance with a further preferred embodiment of the invention, the number of red and/or white blood cells in the detection volume is reduced in order to reduce absorption and scattering of light. For example a mesh with a shutter mechanism can be used for this purpose.

In accordance with a further group of preferred embodiments of the invention, optical elements are used to enhance the collection efficiency of the Raman scattered radiation. This can be done by means of spherical or ellipsoidal mirrors.

In accordance with a further preferred group of embodiments the blood detection volume is located in a cavity of the catheter head through which blood flows. In order to enhance the flow of blood through the detection volume the blood channel through the catheter head can be disposed such to make usage of the Pitot tube effect.

As an alternative to the Raman effect other spectroscopic techniques can be used. For example this can be done by means of infrared light which is directed to the blood detection volume. In this instance the return radiation is analysed by means of infrared absorption spectroscopy which detects changes in the infrared light intensity.

In accordance with a further preferred embodiment of the invention fluorescence spectroscopy is used. In this instance a laser beam or another kind of radiation is directed to the blood detection volume in order to excite molecules to emit induced fluorescence. The detected fluorescence forms the basis for the determination of the at least one property of the blood.

In accordance with a further preferred embodiment of the invention elastic scattering spectroscopy is used. In this case the variations of the reflectance are used to perform the blood analysis.

It is to be noted that the present invention is not restricted to any particular spectroscopic technique but that any type of optical spectroscopy can be used. This includes (i) infra-red spectroscopy, in particular infra-red absorption spectroscopy, Fourier transform infra-red (FTIR) spectroscopy and near infra-red (NIR) diffuse reflection spectroscopy, (ii) scattering spectroscopy techniques, in particularly Raman spectroscopy, stimulated Raman spectroscopy, coherent anti-Stokes Raman spectroscopy (CARS), fluorescence spectroscopy, multi-photon fluorescence spectroscopy and reflectance spectroscopy, and (iii) other spectroscopic techniques such as photo-acoustic spectroscopy, polarimetry and pump-probe spectroscopy. Preferred spectroscopic techniques for application to the present invention are IR absorbance spectroscopy and fluorescence spectroscopy.

In accordance with a further preferred embodiment of the invention the catheter head has means for analysis of the return radiation being adapted to perform a spectroscopic analysis, such as Raman spectroscopic analysis, infra-red absorption spectroscopic analysis, scattering spectroscopic analysis, fluorescence spectroscopic analysis.

In accordance with a further preferred embodiment of the invention the radiation that is directed to the volume of interest is selected to cause molecular vibrational scattering in order to provide the return radiation. For example, the radiation is laser radiation or infrared radiation.

In accordance with a further preferred embodiment of the invention a remote controllable shutter is arranged in front of a mesh. The mesh has a size that prevents red and/or white blood cells to enter the detection volume.

In accordance with a further preferred embodiment of the invention a mirror is used for the radiation and/or the return radiation, the mirror being a spherical mirror or an ellipsoidal mirror.

In accordance with a further preferred embodiment of the invention the catheter head has a first optical wave guide for directing of the laser radiation to the blood detection volume and a second optical wave guide for receiving of the Raman scattered radiation for transmission to the means for spectroscopic analysis.

In accordance with a further preferred embodiment of the invention the first optical wave guide determines an excitation light path and the second optical wave guide determines a detection light path, and further comprising means for decoupling the excitation light path and the detection light path.

In accordance with a further preferred embodiment of the invention the catheter head has means for filtering out of the laser radiation in the detection light path.

In another aspect the invention concerns a catheter system having a catheter head, the catheter comprising at least one optical wave guide for coupling of the catheter head to a Raman laser source and to means for spectroscopic analysis.

In still another aspect the invention concerns an imaging system for catheterisation comprising a catheter system and having display means for display of a blood property being detected by the spectroscopic analysis.

BRIEF DESCRIPTION OF THE DRAWINGS

In the following preferred embodiments of the invention will be described in greater detail by making reference to the drawings, in which.

DETAILED DESCRIPTION

Figure 1:
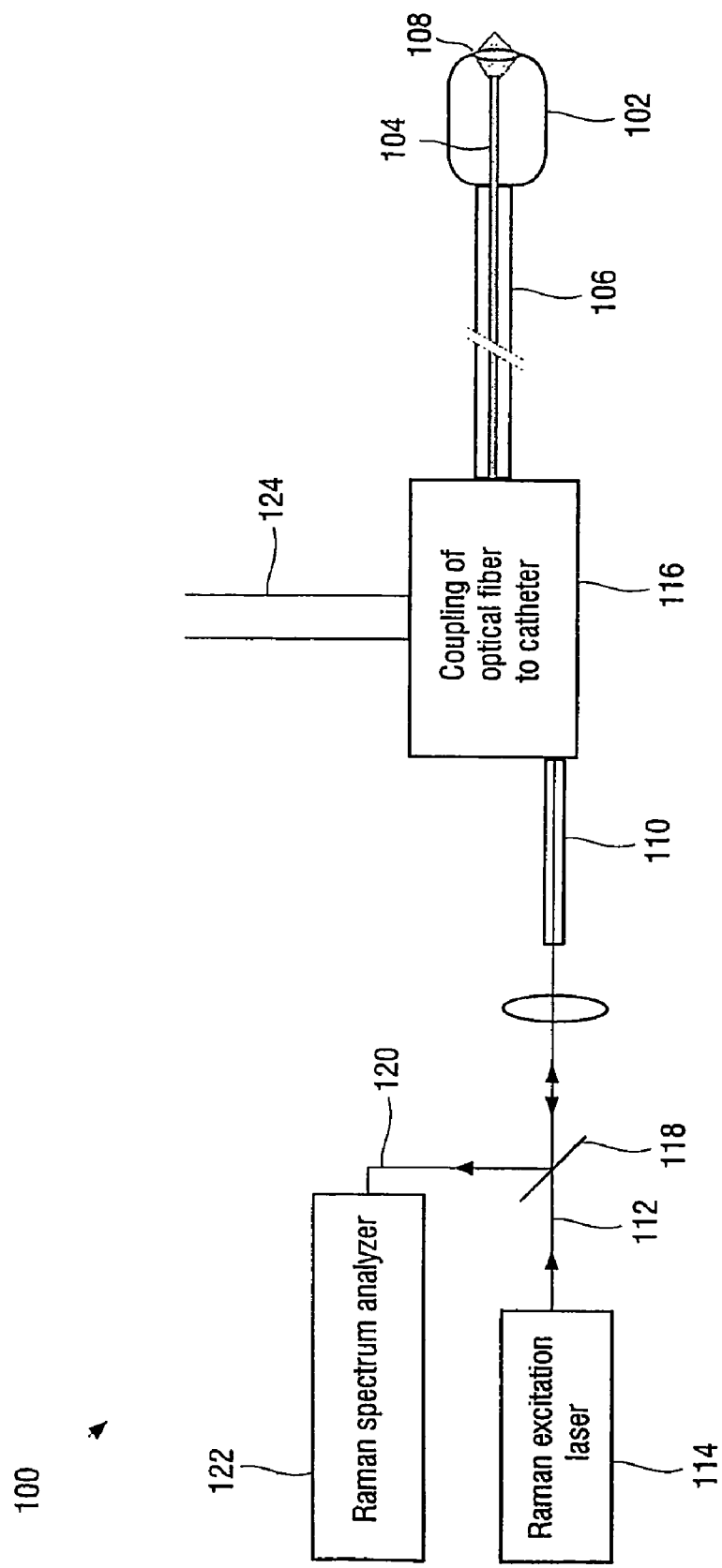
FIG. 1 is a block diagram of a catheter system of the invention.

FIG. 1 shows a catheter system 100 having a catheter head 102. Catheter head 102 comprises optical fibre 104 which extends through catheter 106. Further, catheter head 102 has objective lens 108 for directing of radiation towards a detection volume and for collecting of Raman scattered radiation.

Optical fibre 104 is coupled to optical fibre 110. Optical fibre 110 conducts laser beam 112 provided by Raman excitation laser 114 through connector 116 to optical fibre 104. Laser beam 112 is directed towards a detection volume through objective lens 108. The Raman scattered radiation is collected by objective lens 108 and coupled into optical fibre 104.

The Raman scattered radiation travels through optical fibre 104, connector 116, optical fibre 110 to mirror 118, from where the Raman scattered radiation 120 is provided to Raman spectrum analyser 122. Raman spectrum analyser 122 analyses the spectrum of the received Raman scattered radiation 120 in order to determine one or more blood properties such as the concentrations of glucose, glycohemoglobin, lactate, bilirubin, cholesterol, triglycerides, hemoglobin and blood gases.

Further, a variety of other catheter inputs 124 can be connected to catheter head 102 via connector 116 and catheter 106 depending on the purpose of the catheterisation such as PTCA or others (cf. U.S. Pat. No. 5,938,582 or 6,302,866). Usually each application requires its own special catheter while some functionalities can be combined in specially designed catheters.

Figure 2:
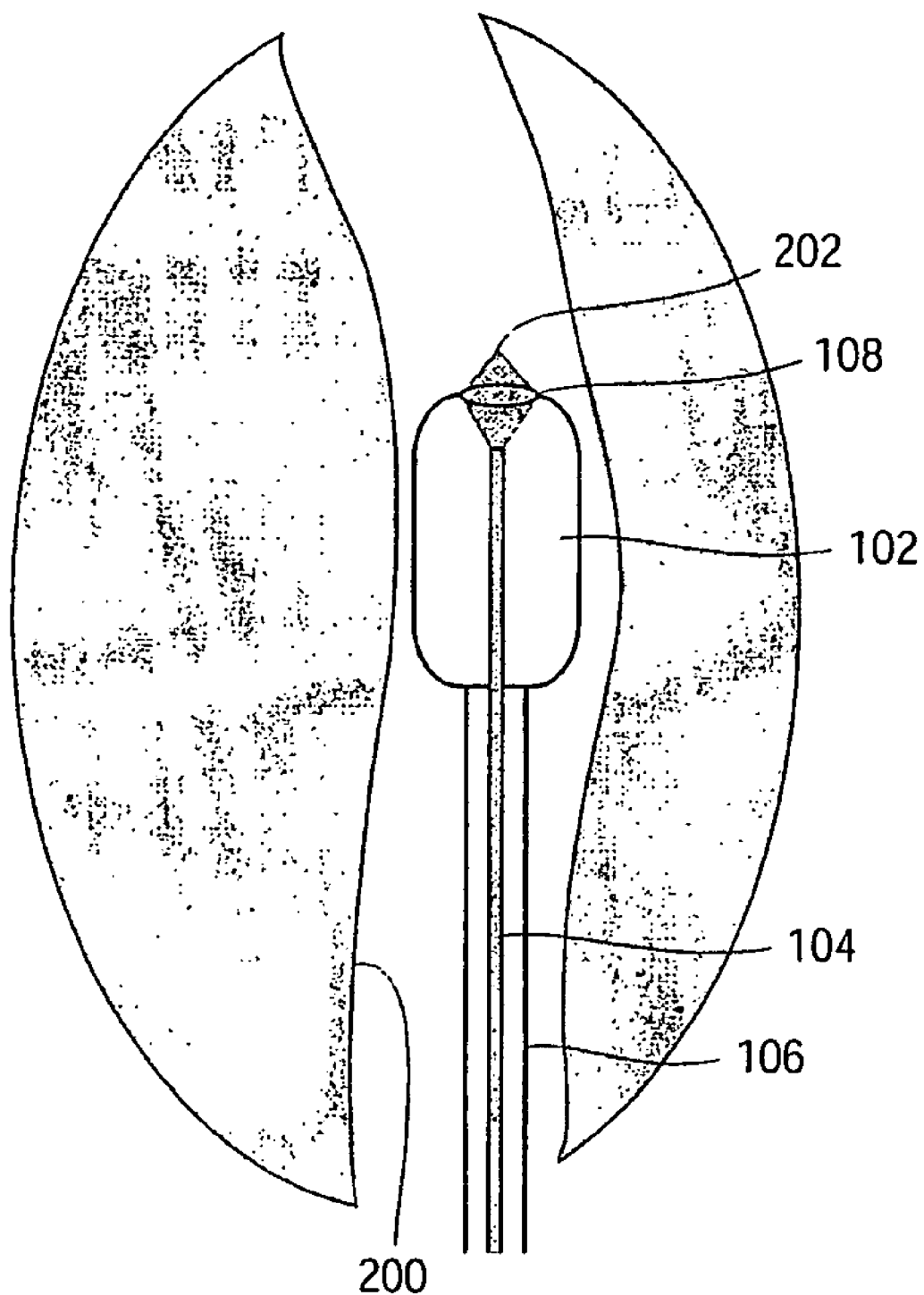
FIG. 2 is illustrative of the catheter head of the catheter system of FIG. 1 in a blood vessel.

FIG. 2 shows catheter head 102 of catheter system 100 of FIG. 1 in operation. Catheter head 102 has been introduced into blood vessel 200 by means of catheter 106. A laser beam is directed through optical fibre 104 to the confocal detection volume 202 which is defined by objective lens 108. Raman radiation is scattered back by the blood flowing through the confocal detection volume 202 which is collected by objective lens 108 and coupled into optical fibre 104.

FIGS. 3 to 13 show various preferred embodiments of catheter heads for usage in a catheter system of the type as shown in FIGS. 1 and 2.

Figure 3:
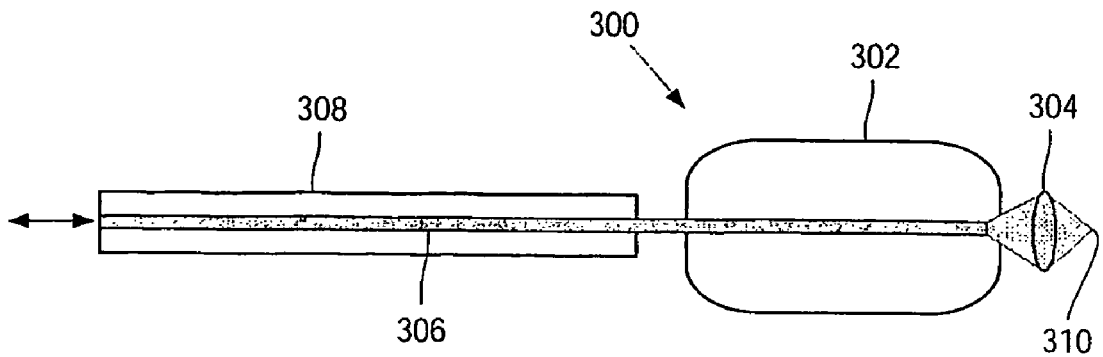
FIG. 3 to 13 show various embodiments of catheter heads.

FIG. 3 shows catheter head 300 which is similar to catheter head 102 of FIGS. 1 and 2. Catheter head 300 has an elongated housing 302 with an opening for receiving objective lens 304. Optical fibre 306 (cf. optical fibre 104 of FIGS. 1 and 2) serves to conduct laser radiation through catheter 308 which is directed through objective lens 304 towards the confocal detection volume 310. Raman radiation which is back scattered from detection volume 310 into the direction of objective lens 304 is coupled back into optical fibre 306 for transmission to the Raman spectrum analyser (c.f. Raman spectrum analyser 122 of FIG. 1). However, it is to be noted that the elongated form of the housing is not essential for the present invention.

In the following preferred embodiments of FIGS. 4 to 12, alike elements will be designated by the same reference numerals as in FIG. 3.

Figure 4:
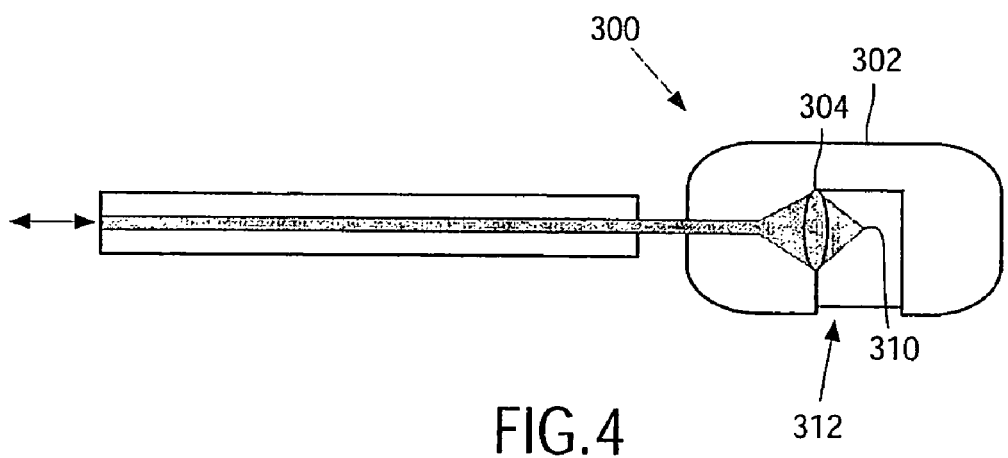

In the embodiment of FIG. 4, a cavity 312 is formed in housing 302. Through an opening which is formed in housing 302 blood can flow into cavity 312. Confocal detection volume 310 is located inside cavity 312. In the example considered here objective lens 304 is arranged on one of the side walls of cavity 312. This way the surface of objective lens 304 is protected against contamination from the vessel walls as the catheter head 300 moves through the vessel.

Figure 5:
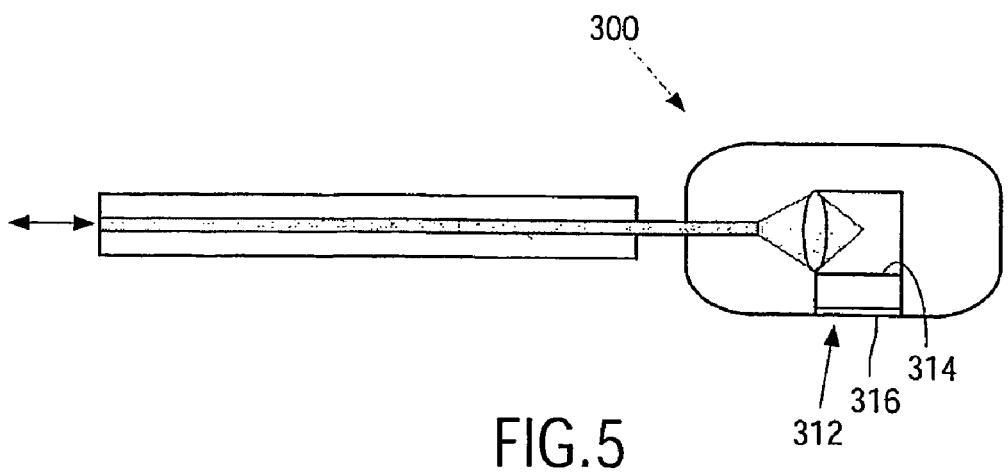

In the embodiment of FIG. 5 mesh 314 is disposed at the opening of cavity 312 towards the blood vessel. Mesh 314 filters out red and/or white blood cells. When mesh 314 is closed only blood plasma enters cavity 312. This reduces the absorption and scattering of the Raman laser light and Raman signal by the red and/or white blood cells.

In order to filter out the red and/or the white blood cells a mesh size of below 5 microns is selected.

In addition shutter 316 can be placed in front of the mesh 314. This prevents the mesh from being contaminated while the catheter head 300 is moved through the blood vessels. Shutter 316 is remote controlled and is only opened before a blood measurement to enable blood flow through cavity 312.

Figure 6:
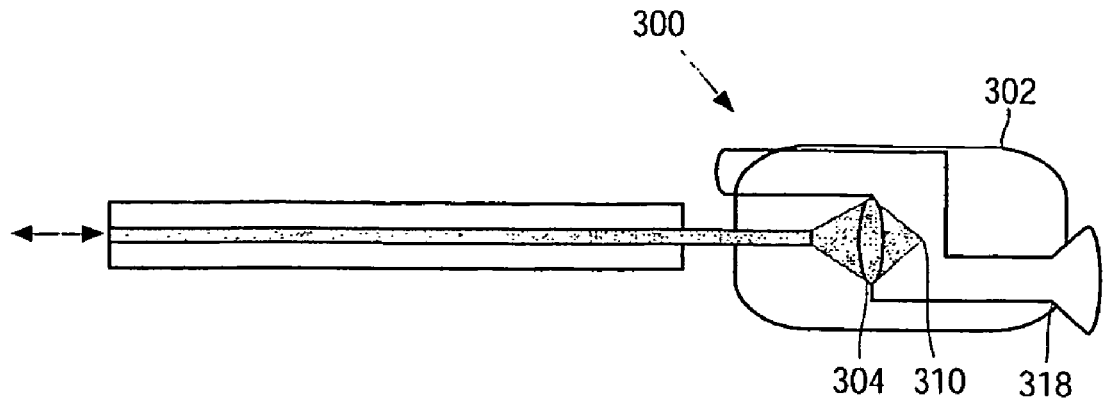
Figure 7:
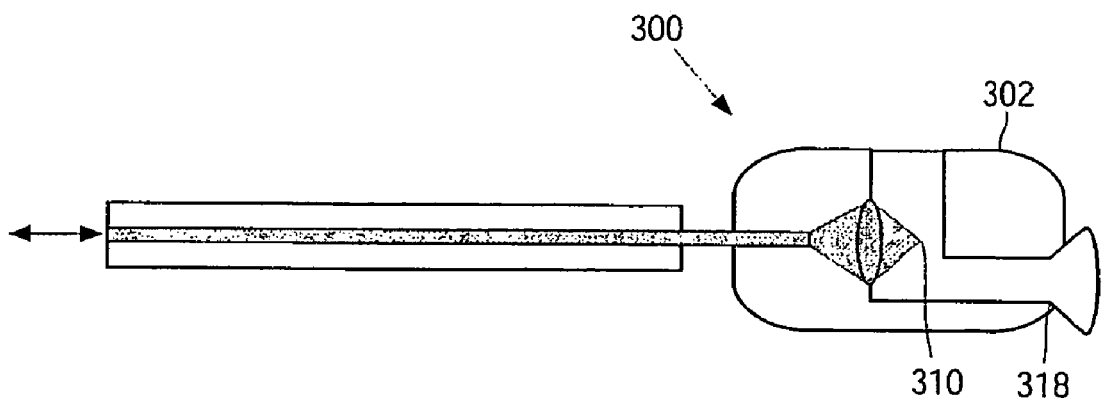

In the embodiment of FIG. 6 a blood channel 318 is formed in housing 302 which enables a flow of blood through catheter head 300 passing by confocal detection volume 310. This has the advantage that the surface of objective lens 304 can be protected against contamination and that the flow of blood through the detection volume 310 is enhanced at the same time.

Channel 318 can be realised by means of a tube running through catheter head 300. Alternatively, it is also possible to use a groove along the side of the catheter head 300. In the preferred embodiment of FIG. 7 the blood flow is further enhanced by using the Pitot tube effect. For this purpose channel 318 has one opening at the front of housing 302 and one opening at the side of housing 302. This way an extra pressure difference is created when the blood flows along housing 302 which enhances the blood flow through channel 318 and through detection volume 310.

Figure 8:
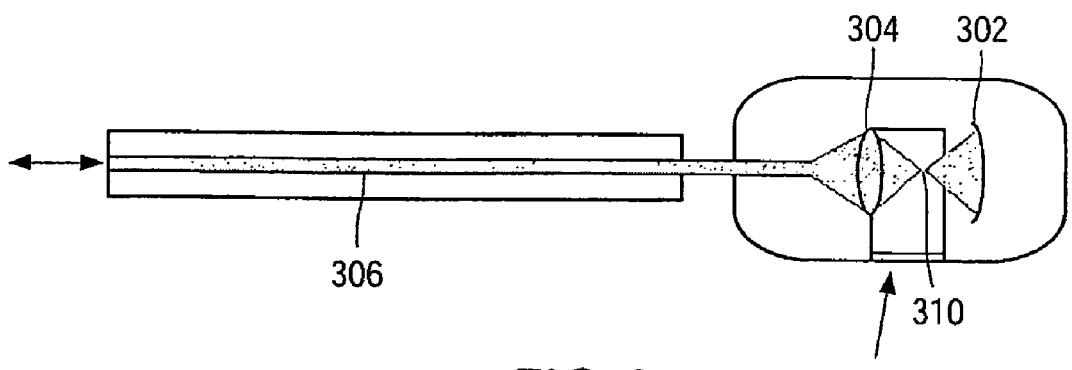

In the preferred embodiment of FIG. 8 a spherical mirror 320 is located opposite to objective lens 304. Detection volume 310 is located within cavity 312 between objective lens 304 and spherical mirror 320. The laser light which is directed towards detection volume 310 through objective lens 304 is reflected back into detection volume 310 by spherical mirror 320. As a consequence Raman scattering takes place twice, once for the original laser beam and once for the reflected laser beam. Further the Raman scattered radiation is also reflected by spherical mirror 320 and collected by objective lens 304; as a result the sensitivity and the Raman signal to noise ratio are substantially increased.

Figure 9:
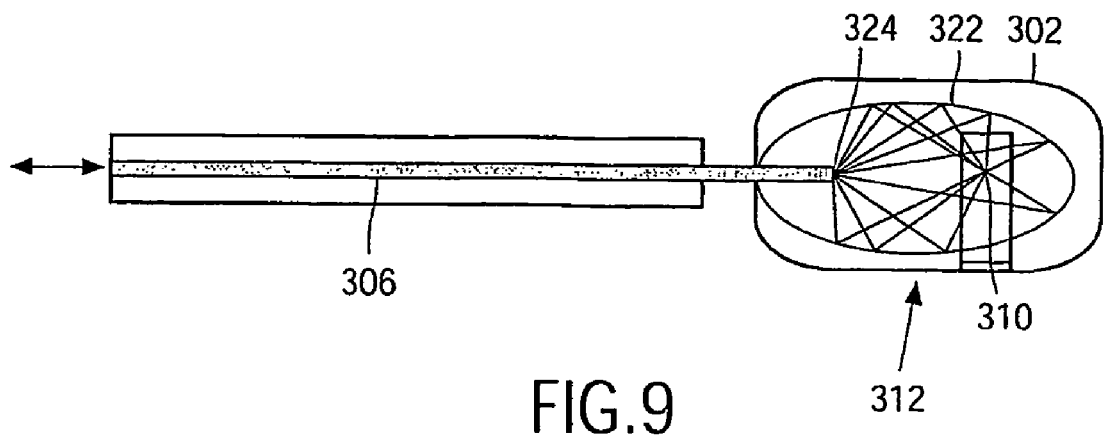

In the embodiment of FIG. 9 an ellipsoidal mirror 322 is disposed within housing 302. Distal end 324 of optical fibre 306 is located at one of the focal points of ellipsoidal mirror 322. Detection volume 310 is located at the other focal point of ellipsoidal mirror 322. Blood flows to the detection volume 310 through cavity 312 which extends into ellipsoidal mirror 322 and prevents a complete flooding of ellipsoidal mirror 322 with blood.

Figure 10:
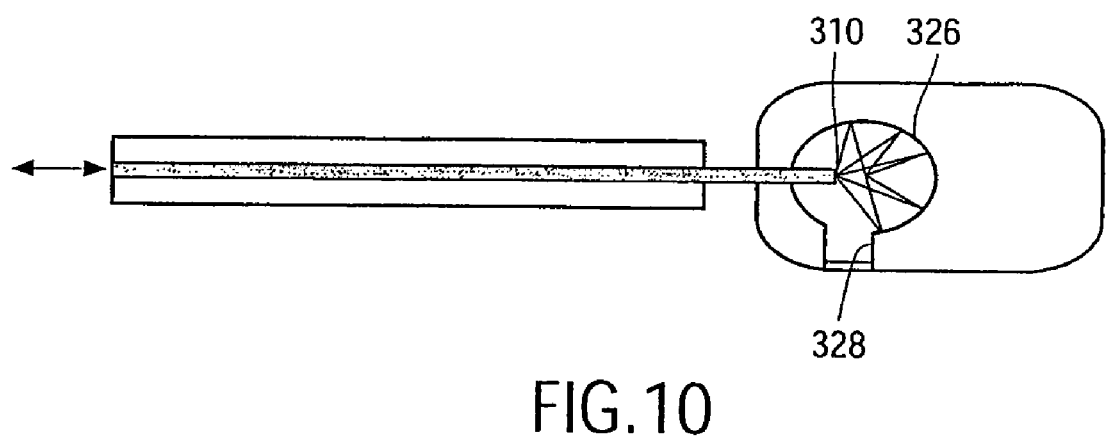

In the embodiment of FIG. 10 mirror 326 is completely filled with blood through opening 328 in housing 302. Mirror 326 can be an ellipsoid or a spherical mirror. In this instance, detection volume 310 is located at the orifice of the optical fibre 306.

Figure 11:
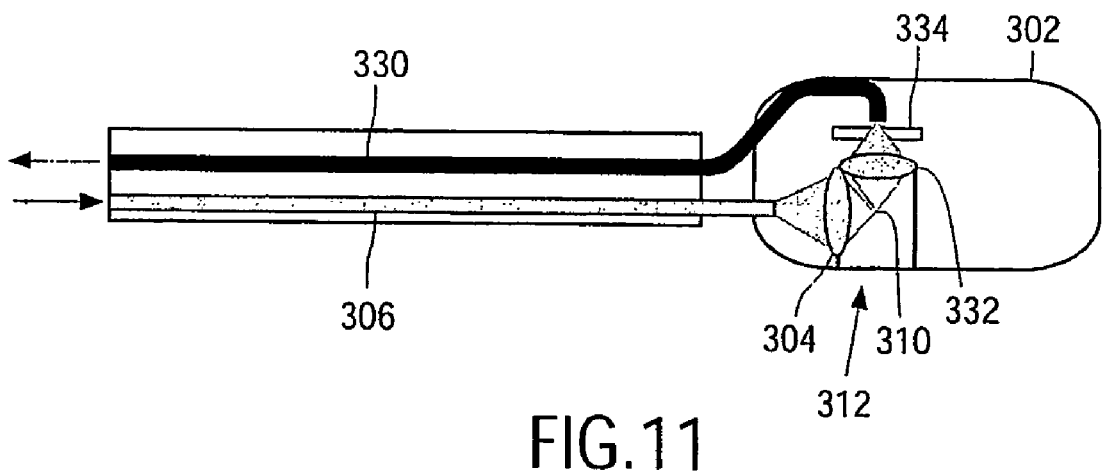

In the preferred embodiment of FIG. 11 separate optical fibers 306 and 330 are used for guiding of laser radiation to detection volume 310 and for transmitting of the Raman scattered radiation back to the Raman spectrum analyser (cf. Raman spectrum analyser 122 of FIG. 1), respectively. Raman scattered radiation is collected by objective lens 332 which is perpendicular to objective lens 304 for decoupling. Alternatively another angle can be used. This way the amount of laser light which is coupled into optical fibre 330 is reduced. For further reduction of the laser light in optical fibre 330 a filter 332 can be located between optical fibre 330 and objective lens 332 to suppress the excitation wavelength. This has the advantage that the Raman scattered radiation is not overlaid by fluorescence.

When only a single optical fibre is used both for the Raman excitation laser beam and the Raman scattered radiation return beam the problem is that the excitation laser beam can create some amount of fluorescence in the optical fibre. This fluorescence has a negative influence on the signal to noise ratio of the Raman signal. By decoupling the Raman excitation laser beam and the return beam this problem is solved as the very low intensity Raman return beam does not create fluorescence in the return optical fibre 330. As a consequence the signal to noise ration is improved in comparison to the embodiments using only a single optical fibre.

Figure 12:
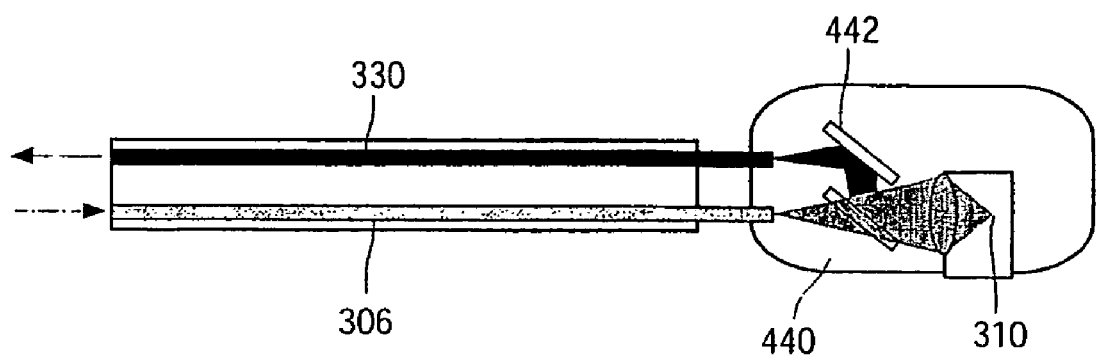

FIG. 12 shows an alternative way of decoupling the Raman excitation laser beam and the return beam. Dichroic mirror 440 is positioned in the light path of the Raman excitation laser beam. At the wavelength of the Raman excitation laser beam, e.g. 785 nm, dichroic mirror 440 is transparent.

The Raman scattered radiation is reflected from dichroic mirror 440 as dichroic mirror 440 is reflective at the wavelength of the Raman scattered radiation, e.g. 800 to 1000 nm. Dichroic mirror 440 reflects the Raman scattered radiation onto mirror 442, which can also be dichroic. From mirror 440 the Raman scattered radiation is coupled into optical fibre 330. No or only a limited fraction of the Raman excitation laser beam is coupled into optical fibre 330 as at least dichroic mirror 440 is transparent to the Raman excitation laser beam.

Figure 13:
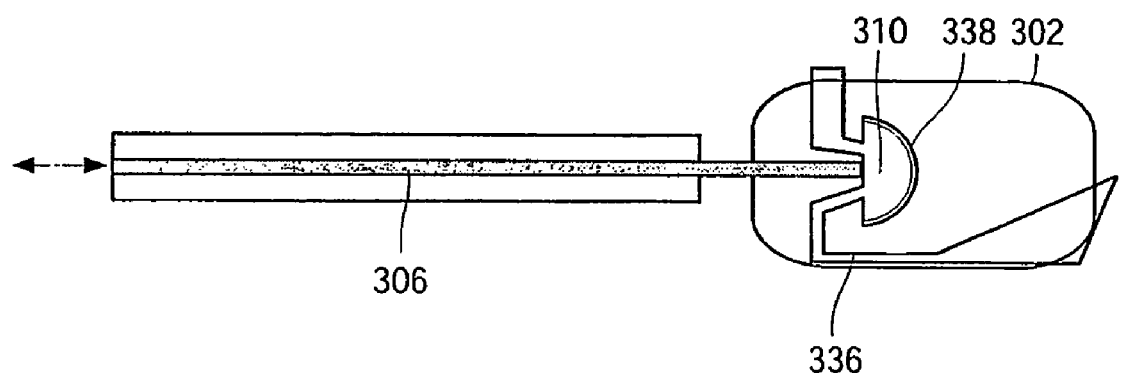

In the embodiment of FIG. 13 blood channel 336 which is arranged in housing 302 has half-round shape 338 around the detection volume 310. The orifice of the optical fibre 306 is located at the centre of the flat side of half-round shape 338. The half-round shape is covered with a reflective coating and acts as a spherical mirror. The diameter of the tubular portion of channel 336 is as small as possible to limit absorption of blood. Again using a Pitot type of tube form enhances the blood flow.

Figure 14:
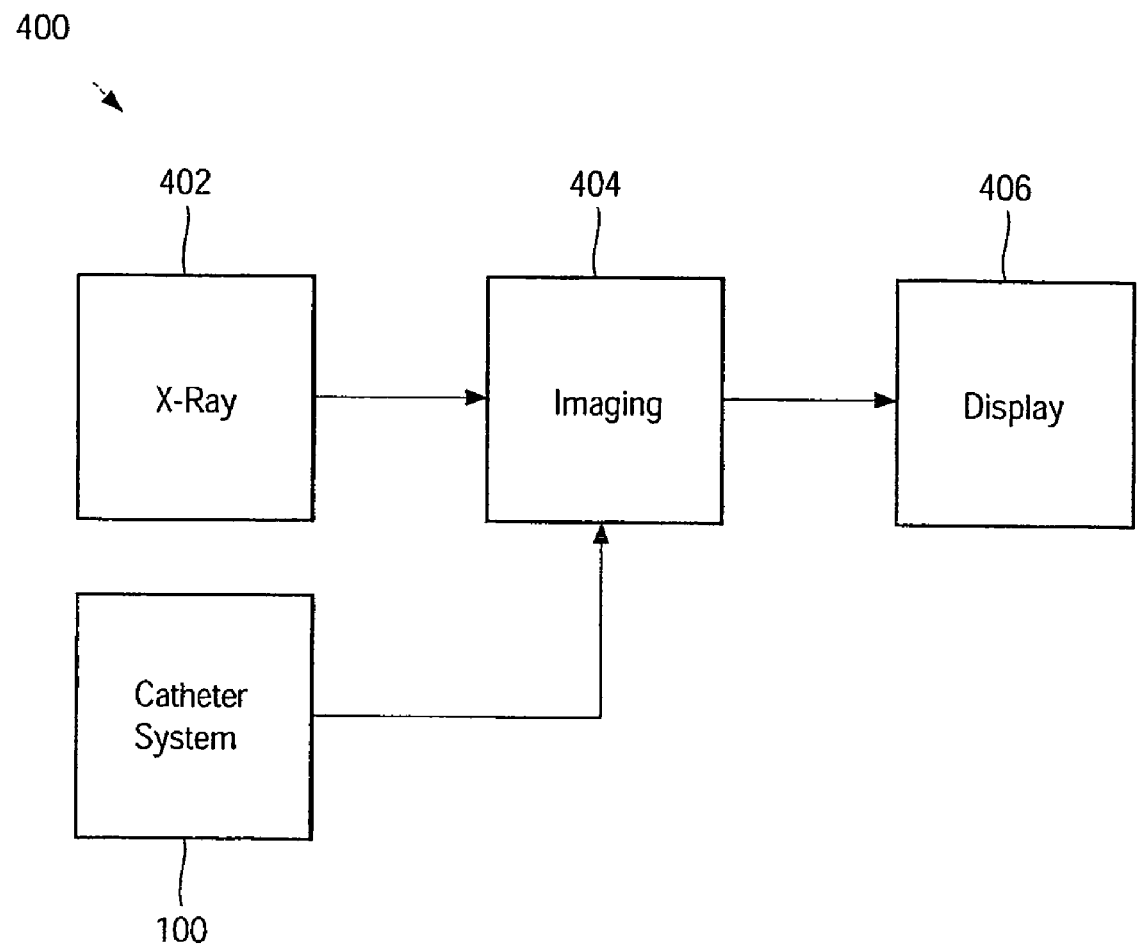
FIG. 14 shows a block diagram of an imaging system for catheterisation.

FIG. 14 shows an imaging system 400 having an X-ray component 402 for acquisition of image data. X-ray component 402 is coupled to imaging component 404 for processing of the image data. The output of imaging component 404 is coupled to display unit 406. Such imaging system are known from the prior art for monitoring of catheterisation. In addition to prior art imaging systems catheter system 100 (cf. FIG. 1) is coupled to imaging component 404. Catheter system 100 provides blood analysis data to imaging component 404. The blood analysis data is integrated into the picture which is generated by imaging component 404 and displayed on display 406. This way an operator is provided with both imaging data as well as chemical analysis data for improved monitoring of the state of the patient's body.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

REFERENCE NUMERALS 100 catheter system
102 catheter head
104 optical fibre
106 catheter
108 objective lens
110 optical fibre
112 laser beam
114 raman excitation laser
116 connector
118 mirror
120 raman scattered radiation
122 raman spectrum analyser
124 catheter inputs
200 blood vessel
202 detector volume
300 catheter head
302 housing
304 objective lens
306 optical fibre
308 catheter
310 detection volume
312 cavity
314 mesh
316 shutter
318 channel
320 spherical mirror
322 ellipsoidal mirror
324 distal end
326 mirror
328 opening
330 optical fibre
332 objective lens
334 filter
336 channel
338 half-round spherical mirror
440 dichroic mirror
442 mirror
400 imaging system
402 x-ray component
404 imaging component
406 display unit

The invention claimed is:

1. A catheter head comprising:
   at least one waveguide for directing radiation to a blood detection volume and for directing of return radiation to a spectroscopic analyzer that determines at least one property of the blood;
   an objective lens for receiving the return radiation from the blood detection volume;
   a housing, the detection volume being located inside a cavity of the housing, the housing having a sidewall with an opening therethrough to enable the blood to flow into the cavity;
   a concave mirror at least partially forming an end of the cavity opposite to an end of the waveguide, the concave mirror being positioned relative to the at least one waveguide such that radiation emitted from the at least one waveguide:
   (1) in part is scattered by the blood, which scattered radiation in part is reflected by the blood back to the end of the at least one waveguide and which scattered radiation in part passes through the blood in the cavity to the concave mirror, is reflected by the concave mirror, and passes back through the blood in the cavity to the end of the waveguide and
   (2) in part passes through the blood in the cavity is reflected by the concave mirror back in to the blood in the cavity and is scattered by the blood and the scattered radiation passes to the end of the at least one waveguide.

2. The catheter head of claim 1 wherein the at least one waveguide is a single wave guide for guiding of the radiation to the blood detection volume and for receiving the return radiation for transmission to the means for spectroscopic analysis.

3. The catheter head of claim 1, wherein the objective lens is in front of the wave guide and is made from a material that reflects Raman scattered radiation.

4. The catheter head of claim 1, further comprising a channel formed through the housing and defining at least in part the cavity, wherein the channel has at least two openings with a first opening along the sidewall.

5. The catheter head of claim 1, wherein the concave mirror includes a spherical mirror configured to reflect the Raman scattered radiation back into the blood detection volume.

6. The catheter head of claim 1, wherein the concave mirror includes an ellipsoidal mirror, the blood detection volume comprising one of the focal points of the ellipsoidal mirror and a distal end of the wave guide being located at the other focal point of the ellipsoidal mirror, the mirror forming the cavity.

7. The catheter head of claim 1, further comprising a dichroic mirror that allows the radiation to pass therethrough and reflects the return radiation.

8. The catheter head of claim 1, further including:
a shutter which is controlled remote from the catheter head to selectively permit and prevent access to the blood detection volume.

9. The catheter head of claim 1 further including:
a mesh across the opening in the side wall, the mesh having openings sized to prevent at least one of red and white blood cells from entering into the cavity.

10. A catheter head comprising:
at least one waveguide for directing of radiation to a bodily fluid detection volume and for directing of return radiation to a spectroscopic analyzer that determines at least one property of the bodily fluid;
an objective lens for receiving of return radiation from the detection volume; and
a housing, the detection volume being located along a channel through the housing, the channel having at least two openings and defining a non-linear path through the housing, the detection volume being defined in the non-linear channel.

11. The catheter head of claim 10, wherein at least a portion of the channel is coated to provide the reflective surface.

12. The catheter head of claim 10, wherein an end of the cavity opposite to an end of the waveguide has a reflective surface thereon.

13. A method of in vivo analysis of blood, the method comprising:
positioning a catheter head in blood in vivo;
capturing a plasma portion of the blood in a fluid detection volume of a housing of the catheter head, including preventing at least one of red and white blood cells from entering the fluid detection volume;
generating a Raman excitation radiation;
guiding the Raman excitation radiation through the catheter head into the fluid detection volume to produce scattered radiation;
reflecting the scattered radiation using a dichroic mirror; and
guiding the scattered radiation through the catheter head to a spectroscopic analyzer to determine at least one property of the plasma portion of the blood.

14. The method of claim 13, further comprising providing selective access to the fluid detection volume using a shutter that is remotely controlled.

15. The method of claim 13, wherein the guiding of the Raman excitation radiation and the guiding of the scattered radiation is performed by separate waveguides in the catheter head.

16. A method of in vivo analysis of a bodily fluid, the method comprising:
positioning in vivo a catheter head in proximity to the bodily fluid;
drawing a portion of the bodily fluid through a housing along a non-linear path;
generating a Raman excitation radiation;
guiding the Raman excitation radiation through the catheter head into a fluid detection volume defined in the non-linear path to produce scattered radiation; and
guiding the scattered radiation through the catheter head to a spectroscopic analyzer to determine at least one property of the bodily fluid.

17. The method of claim 16, wherein drawing the portion of the bodily fluid along the non-linear path includes using a pitot tube effect, wherein the housing has at least two openings for flow of the portion of the bodily fluid.

18. The method of claim 16, further comprising reflecting at least a portion of the scattered radiation into a waveguide that is guiding the scattered radiation through the catheter head.

19. The method of claim 16, further comprising preventing at least one of red and white blood cells from entering the fluid detection volume using a mesh.

* * * * *